United States Patent
Scherer et al.

(10) Patent No.: US 6,762,315 B1
(45) Date of Patent: Jul. 13, 2004

(54) METHOD FOR PRODUCING (1,1′,4,1″)-TERPHENYL COMPOUNDS

(75) Inventors: Stefan Scherer, Büttelborn (DE); Steffen Haber, Landau/Pfalz (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/914,478

(22) PCT Filed: Feb. 2, 2000

(86) PCT No.: PCT/EP00/00834
§ 371 (c)(1), (2), (4) Date: Aug. 24, 2001

(87) PCT Pub. No.: WO00/50375
PCT Pub. Date: Aug. 31, 2000

(30) Foreign Application Priority Data

Feb. 24, 1999 (DE) .......................... 199 07 904

(51) Int. Cl.$^7$ .......................... C07C 69/76; C07C 63/33
(52) U.S. Cl. .......................... 560/59; 562/469
(58) Field of Search .......................... 560/59; 562/469

(56) References Cited

U.S. PATENT DOCUMENTS 5,693,611 A   12/1997   Henle et al.
5,948,753 A  * 9/1999   Balkovec et al.

FOREIGN PATENT DOCUMENTS

| EP | 0 561 639 | 9/1993 |
| EP | 0 637 624 | 2/2001 |
| WO | WO 94/25050 | 11/1994 |

OTHER PUBLICATIONS

Handbook of Chemistry and Physics, 70th edition, 1989, CRC Press, Florida, p. C–133.*
Miyaura et al, Palladium–Catalyzed Cross–Coupling Reactions of Organoboron Compounds, 1995, Chemical Reviews, 95, pp. 2457–2483.*
International Search Report for PCT/EP Application No. 00/00834, mail date of Jun. 7, 2000.

* cited by examiner

Primary Examiner—Gary Geist
Assistant Examiner—Paul A. Zucker

(74) Attorney, Agent, or Firm—Scott E. Hanf; Anthony A. Bisulca

(57) ABSTRACT

The invention relates to a method for producing [1,1′:4′,1″]-terphenyl compounds of the formula (1)

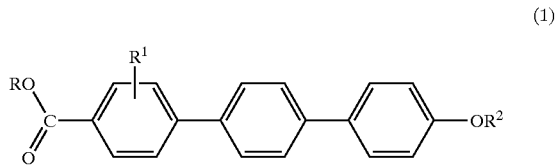

which comprises reacting a metal aryl of the formula (2)

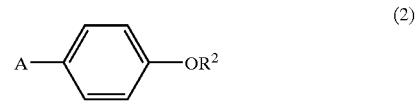

with a boric ester at −80 to 40° C. in the presence of an inert solvent, converting the reaction product by hydrolysis into a boronic acid of the formula (3)

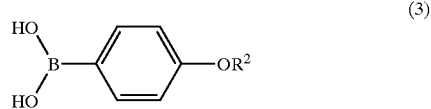

reacting the boronic acid, a boronic anhydride obtainable from boronic acid by elimination of water, or a mixture of boronic acid and boronic anhydride, with an alcohol, and reacting the boronic ester formed thereby with a biphenyl compound of the formula (4)

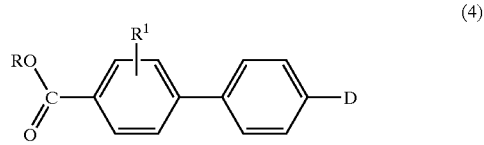

at 40 to 180° C. in the presence of a catalyst, of an acid-binding agent and of a polar solvent.

11 Claims, No Drawings

METHOD FOR PRODUCING (1,1',4, 11")-TERPHENYL COMPOUNDS

This application is a 371 of PCT/EP00/00834 filed Feb. 2, 2000.

BACKGROUND OF THE INVENTION

The present invention relates to a method for producing [1,1':4',1"]-terphenyl compounds substituted in the 4" position.

4"-Alkoxyterphenyl-4-carboxylic acids whose alkoxy group contains an alkyl radical of medium chain length are used in conjunction with the echinocandin B macrocycle as building blocks for producing active ingredients with antibiotic, in particular antifungal, properties.

These active ingredients display a novel principle of action and are therefore of particular interest (WO 94/25050 and EP 0 561 639).

The 4"-substituted p-terphenyl to be emphasized from the group thereof is 4"-n-pentoxy-[1,1':4',1"]-terphenyl-4-carboxylic acid, which leads, after coupling with the echinocandin B macrocycle, to a product with excellent properties.

WO 94/25050 describes a multistage method for producing 4"-n-pentoxy-[1,1':4',1"]-terphenyl-4-carboxylic acid (cf. pages 28 and 29 part A, part B and part C).

In a first step, 4'-bromo-4-hydroxybiphenyl is reacted with an n-pentyl halide to give the corresponding 4'-bromo-4-n-pentoxybiphenyl. The 4'-bromo-4-n-pentoxybiphenyl is reacted in a second step with n-butyllithium at −78° C. to form, by transmetallation, 4'-lithium-4-n-pentoxybiphenyl which, in another step likewise at −78° C., is reacted with triisopropyl borate. Hydrolysis and work-up result in 4'-n-pentoxybiphenyl-4-boronic acid which is reacted in further steps with 4-iodobenzoic acid in a standard Suzuki coupling. The 4"-n-pentoxy[1,1':4',1"]-terphenyl-4-carboxylic acid is obtained as crude product which is purified by chromatography on silica gel.

The mode of synthesis is depicted diagrammatically in simplified form below

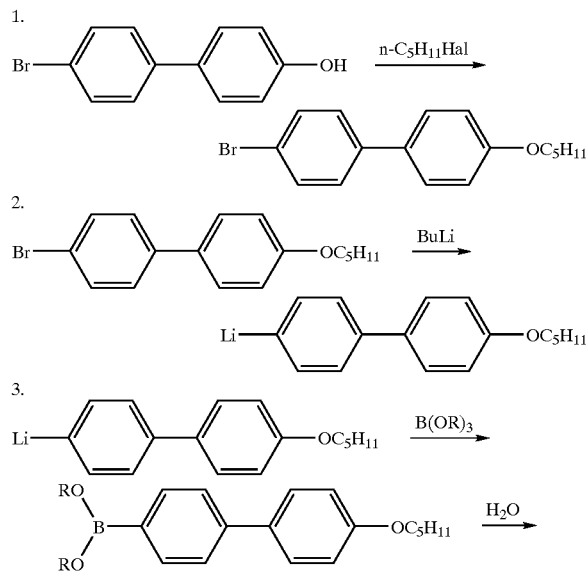

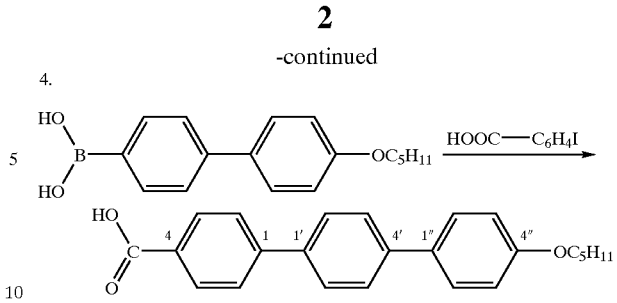

WO 94/25050 states yields only for the stages (part A and part B) up to formation of 4-(4-n-pentyloxyphenyl) phenylboronic acid. There is no statement of yield in part C, which relates to the production of 4"-n-pentoxy-[1,1':4',1"]-terphenyl-4-carboxylic acid.

EP 0 561 639 discloses the production of methyl 4"-n-pentoxy-[1,1':4',1"]-terphenyl-4 carboxylate using the aforementioned reaction steps 2, 3 and 4, employing methyl 4-iodobenzoate in place of 4-iodobenzoic acid in step 4. The yield of 4'-n-pentoxybiphenyl-4-boronic acid is 44% and in the reaction thereof with methyl 4-iodobenzoate is 64% (cf. statements on page 26, table 15 and 16, in each case second line across), which means that the overall yield is only 28.2% based on 4'-bromo-4-n-pentoxybiphenyl.

The method described above has several disadvantages. On the one hand, it is necessary to start from a very pure 4'-bromo-4-hydroxybiphenyl, which ought to contain the minimum amount of Br positional isomers in order to comply with the required isomer quality in the final product. On the other hand, the transmetallation in step 2 is rather complicated because it must be carried out at very low temperatures. If this reaction is not maintained in a particular temperature range and/or if the reaction times are too long, the corresponding 4,4"-di-n-pentoxy-[1,1':1",4",1"']-quaterphenyl is produced as a result of dimerization. This compound can, however, be removed from the desired final product only in a very complicated way. The reaction in step 3 is also carried out at very low temperature. A further disadvantage is that 4"-pentoxy-[1,1':4',1"]-terphenyl-4-carboxylic acid is evidently obtained as very impure crude product which must be purified by chromatography on silica gel.

SUMMARY OF THE INVENTION

In view of this, the object is to provide a method which avoids the disadvantages described above and can be carried out with acceptable effort.

This object is achieved by a method for producing [1,1':4', 1"]-terphenyl compounds with the formula

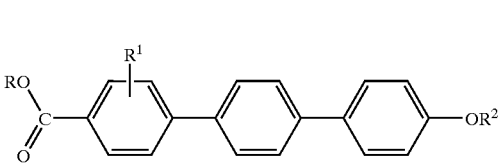

(1)

in which R is hydrogen or a straight-chain or branched $C_1$–$C_4$-alkyl radical, in particular hydrogen, a $C_1$–$C_2$-alkyl radical or $C(CH_3)_3$, $R^1$ is hydrogen, a straight-chain or branched $C_1$–$C_4$-alkyl radical or a straight-chain or branched $C_1$–$C_4$-alkoxy radical, in particular hydrogen, a $C_1$–$C_2$-alkyl radical or $C_1$–$C_2$-alkoxy radical, preferably hydrogen, and $R^2$ is hydrogen, a straight-chain $C_1$–$C_{12}$-alkyl radical, an unsubstituted phenyl radical, a phenyl radical which is substituted by one or two $C_1$–$C_4$-alkyl groups or $C_1$–$C_4$-alkoxy groups, or a radical —$(CH_2)_xOR^3$ in which x is an integer from 1 to 4 and $R^3$ is a straight-chain or branched $C_1$–$C_4$-alkyl radical, in particular a straight-chain $C_1$–$C_8$-alkyl radical, an unsubstituted phenyl radical or a radical —$(CH_2)_xOR^3$, in which x is an integer from 1 to 4 and $R^3$ is a straight-chain or branched $C_1$–$C_4$-alkyl radical, preferably a straight-chain $C_1$–$C_6$-alkyl radical or a radical —$(CH_2)_xOR^3$ in which x is an integer from 1 to 2 and $R^3$ is a straight-chain or branched $C_1$–$C_4$-alkyl radical.

It comprises reacting a metal aryl of the formula

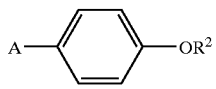

(2)

in which A is a monovalent metal or MeX, where Me is a divalent metal and X is Cl, Br or I, and $R^2$ is A or a trisubstituted silyl radical, or has the meaning indicated in formula (1), excepting hydrogen, with a boric ester at –80 to 40° C. in the presence of an inert solvent, converting the reaction product by hydrolysis into a boronic acid of the formula

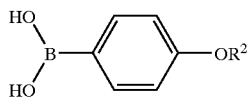

(3)

reacting the boronic acid, a boronic anhydride obtainable from boronic acid by elimination of water, or a mixture of boronic acid and boronic anhydride, with an alcohol, and reacting the boronic ester formed thereby with a biphenyl compound of the formula

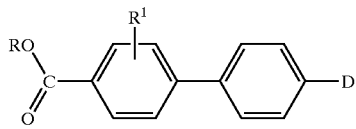

(4)

in which R and $R^1$ have the meaning indicated in formula (1), and D is Cl, Br, I, $O_3S$—$C_nF_{2n+1}$, where n is an integer from 1 to 4, or $N_2^+Y^-$ where $Y^-$ is $ClO_4^-$, $BR_4^-$ or $HSO_4^-$, at 40 to 180° C. in the presence of a catalyst and of a polar solvent.

The method of the invention is depicted diagrammatically below in simplified form

I.

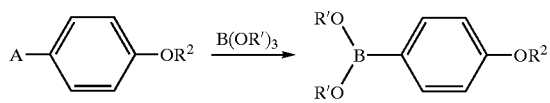

II.

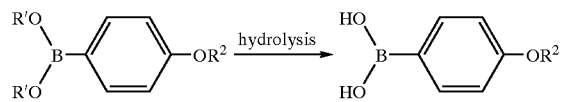

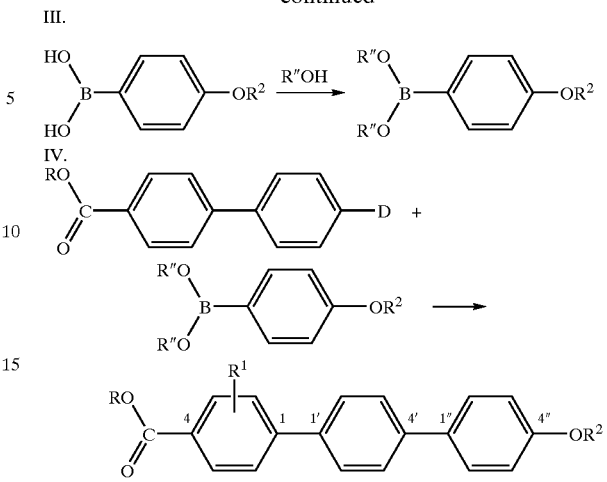

The metal aryl of the formula (2) can be prepared be reacting a benzene derivative appropriately halogenated in the p position for example with Mg or an Li alkyl. There is no formation of a quaterphenyl compound which can be separated from the desired final product only with difficulty. The reaction of the metal aryl with boric ester does not in any case require the low temperatures indicated in WO 94/25050. Grignard compounds allow a reaction at distinctly higher temperatures than indicated in WO 94/25050.

A metal aryl of the formula (2) in which A is Li, Na, K, MgX or ZnX, in particular Li, MgX or ZnX and X is Cl, Br or I, in particular Cl or Br, is normally employed.

The method is particularly simple when a metal aryl of the formula (2) in which A is MgCl, MgBr or MgI, in particular MgCl or MgBr, preferably MgCl, is employed.

As already mentioned above, a metal aryl of the formula (2) in which $R^2$ is A or a trisubstituted silyl radical, or has the meaning indicated in the compound of the formula (1), but in this case cannot be hydrogen, is employed.

If it is intended to produce a terphenyl compound of the formula (1) in which $R^2$ is hydrogen, it is possible to start from a metal aryl (2) in which $R^2$ is A or the trisubstituted silyl radical, and to obtain the appropriate phenolic terphenyl compound by the subsequent work-up of the reaction product.

The trisubstituted silyl radical in the metal aryl is a radical $SiR^4R^5R^6$ in which the radicals $R^4$, $R^5$ and $R^6$ are identical or different and are a phenyl radical or a $C_1$–$C_4$-alkyl radical, in particular are the same and are a $C_1$–$C_4$-alkyl radical. The silyl radical acts as protective group which can easily be eliminated after the reaction to form the appropriate phenolic group. A particularly suitable trisubstituted silyl radical is the $Si(CH_3)_3$ radical.

A boric ester $B(OR')_3$ in which R' is identical to or different from one another and is a straight-chain or branched $C_1$–$C_8$-alkyl radical, a phenyl radical which is unsubstituted or substituted by one or two $C_1$–$C_4$-alkyl groups or $C_1$–$C_4$-alkoxy groups, in particular a straight-chain or a branched $C_1$–$C_4$-alkyl radical, a phenyl radical which is unsubstituted or substituted by one or two $C_1$–$C_4$-alkyl groups, preferably a straight-chain or branched $C_1$–$C_4$-alkyl radical or an unsubstituted phenyl radical, particularly preferably a straight-chain or branched $C_1$–$C_4$-alkyl radical, is employed.

Since the boric esters whose R' radicals are identical can be obtained particularly readily, the boric esters of the aforementioned type employed in a large number of cases will have identical R' radicals. Examples of such boric esters are trimethyl borate, triethyl borate, tri-n-propyl borate, triisopropyl borate, tri-n-butyl borate and triisobutyl borate.

The reaction of the metal aryl with the boric ester is, as already mentioned at the outset, carried out at −80 to +40° C., in particular −70 to 10° C., preferably −40 to 0° C. The inert solvent used is, for example, a dialkyl ether having 1 to 4 carbon atoms in each alkyl radical, a cycloaliphatic ether having 4 to 5 carbon atoms in the ring, for example tetrahydrofuran or 1,4-dioxane, a formaldehyde dialkyl acetal, a 1,2-dialkyl glycol ether having 1 to 4 carbon atoms in each alkyl radical, a mixture thereof or a mixture thereof with toluene, in particular a dialkyl ether having 1 to 4 carbon atoms in each alkyl radical, tetrahydrofuran, a 1,2-dialkyl glycol ether having 1 to 4 carbon atoms in each alkyl radical, a mixture thereof or a mixture thereof with toluene, preferably tetrahydrofuran, dibutyl glycol ether, methyl tert-butyl ether, diethyl ether, diisopropyl ether, di-n-butyl ether a mixture thereof or a mixture thereof with toluene.

The reaction of the boric ester with the metal aryl leads to a salt-like adduct (borate salt). After the reaction is complete, the reaction product which contains, were appropriate, the radical A or the trisubstituted silyl radical as radical $R^2$, and any unreacted metal aryl which is still present, are decomposed by bringing the reaction mixture into contact with water or a water/ice mixture. The hydrolysis of the reaction product takes place very quickly, as does that of the metal aryl, because both the salt-like adduct and the metal aryl react very rapidly with water even at low temperatures. This leads to formation of the boronic acid (3), and salts derived from the reaction product and, where appropriate, from hydrolyzed metal aryl which is likewise still present are produced.

In order to dissolve salts, in particular basic salts, the resulting aqueous mixture is acidified, for example by adding a mineral acid, in particular hydrochloric acid or sulfuric acid. It is advisable to adjust a pH of from 0 to 4, in particular 0.5 to 3, preferably 1 to 2, to ensure complete dissolution of the salts.

A phase separation is then carried out, and the organic phase containing the inert solvent and the boronic acid is separated off. If required, the phase separation can be assisted by adding a suitable inert solvent, for example ether, methylene chloride, chloroform, toluene, chlorobenzene.

The organic phase which has been separated off is mixed with water in order to dissolve any salts still present, and the inert solvent and the solvent employed where appropriate to assist the phase separation are distilled off.

This results in the boronic acid as a solid. It is filtered off and dried. If the drying is carried out at temperature ±30, in particular ±50° C., the boronic acid starts to eliminate water to form the corresponding anhydride. Formation of the boronic anhydrides depends on the one hand on the temperature level, and on the other hand on the time during which the boronic acid is exposed to the temperature. High temperatures and long exposure times favor formation of boronic anhydrides.

If it is desired to obtain the boronic acid, it is advisable to carry out the drying at low temperatures and under vacuum.

It is also possible to hydrolyze the boronic anhydride for example with an aqueous alkali and to liberate the boronic acid by subsequent acidification of the aqueous solution containing salt of boronic acid.

In a large number of cases there is formation of a mixture of boronic acid and boronic anhydride. The boronic anhydride comprises cyclic anhydrides, in particular trimeric boronic anhydride. It is also possible in some circumstances for mixtures of anhydrides possibly to form. The boronic acid, the boronic anhydride and the mixture of boronic acid and boronic anhydride can be, if required, purified by recrystallization in a suitable solvent for example aliphatic, cycloaliphatic and/or aromatic hydrocarbons.

In the following step, the boronic acid, the boronic anhydride or the mixture containing boronic acid and boronic anhydride is reacted with an alcohol. This esterification takes place by conventional methods. It is unnecessary to add a catalyst, for example an acid. It is possible that the boronic acid, the boronic anhydride or the mixture of boronic acid and boronic anhydride acts as catalyst. The esterification is normally allowed to proceed at 50 to 150° C., in particular 60 to 140° C.

In order to favor the reaction, it is advisable to remove the water formed as a result of the esterification. This can take place, for example, by azeotropic distillation to remove water or by addition of dehydrating agents, for example orthoformic esters. Suitable entrainers for azeotropic removal of water are, for example, aliphatic or aromatic hydrocarbons, chlorinated aliphatic or aromatic hydrocarbons, ethers or ketones. Without making any claim to completeness, mention may be made of pentane, hexane, heptane, cyclopentane, cyclohexane, toluene, xylene, ethylbenzene, mesitylene, dichloromethane, chloroform, carbon tetrachloride, trichloroethylene, chlorobenzene, dichlorobenzene, chlorotoluene or dichlorotoluene as entrainers.

The alcohol employed is a $C_1$–$C_8$ alkyl alcohol, a $C_2$–$C_6$-alkane-1,2-diol, a $C_3$–$C_6$-alkane-1,3-diol, a $C_4$–$C_6$-alkane-1,4-diol or 1,2-dihydroxybenzene, in particular a $C_1$–$C_8$-alkyl alcohol, a $C_2$–$C_6$-alkane-1,2-diol or a $C_3$–$C_6$-alkane-1,3-diol, preferably a $C_1$–$C_4$-alkyl alcohol, a $C_2$–$C_4$-alkanediol or a $C_3$–$C_5$-alkane-1,3-diol.

Examples of alkyl alcohols are methanol, ethanol, n-propanol, i-propanol, n-butanol, i-butanol, n-pentanol, 2-methylpentanol, n-hexanol, 2-ethylhexanol, in particular methanol, ethanol, n-propanol, i-propanol, n-butanol and i-butanol.

Examples of suitable alkanediols are ethylene glycol, propane-1,3-diol and 2,2-dimethylpropane-1,3-diol (neopentyl glycol).

The reaction with the alcohol results in formation of the corresponding boronic ester, which is then reacted with the biphenyl compound of the formula (4) in the presence of a catalyst, of an acid-biding agent and of a polar solvent.

However, in place of the boronic ester, it is also possible to employ the boronic acid of the formula (3), the boronic anhydride obtainable from the boronic acid by elimination of water, or the mixture of boronic acid and boronic anhydride, in this reaction and thus dispense with the preparation of the boronic ester by reaction of the boronic acid, of the boronic anhydride or of the mixture of boronic acid and boronic anhydride with the alcohol.

The reaction of the boronic ester or of the boronic acid, the boronic anhydride or the mixture of boronic acid and boronic anhydride takes place —as already mentioned—at 40 to 180° C., in particular 50 to 130° C., preferably 60 to 120° C. Acid-binding agents which can be used are amines, for example, aliphatic amines, in particular trialkylamines, basic salts of organic and inorganic acids, in particular alkali metal salts and alkaline earth metal salts of organic and inorganic acids, for example Na acetate, K acetate, $Na_3PO_4$, $K_3PO_4$, $NaHCO_3$, $KHCO_3$, $Na_2CO_3$, $K_2CO_3$, $MgCO_3$, $CaCO_3$, or alkali metal oxides, alkali metal hydroxides, alkaline earth metal oxides, alkaline earth metal hydroxides, for example NaOH, KOH, $Mg(OH)_2$ or $Ca(OH)_2$.

Very suitable acid-binding agents have proved to be alkali metal bicarbonates, alkali metal carbonates, alkaline earth metal bicarbonates and alkaline earth metal carbonates, in particular $Na_2CO_3$ and $K_2CO_3$, preferably $Na_2CO_3$. The biphenyl compound of the formula 4 which is particularly employed is that in which R is hydrogen or a straight-chain or branched $C_1$–$C_4$-alkyl radical, in particular hydrogen, a $C_1$–$C_2$-alkyl radical or $C(CH_3)_3$, preferably $CH_3$ or $C(CH_3)_3$, $R^1$ is hydrogen or a straight-chain or branched $C_1$–$C_4$-alkyl radical or $C_1$–$C_4$-alkoxy radical, in particular hydrogen, a $C_1$–$C_2$-alkyl radical or $C_1$–$C_2$-alkoxy radical, and D is Cl, Br, I or $N_2^+Y^-$, in particular Cl, Br or I, preferably Br or I.

If is possible to use as polar solvent a protic and aprotic dipolar solvent, in particular an alcohol, a sulfoxide, a sulfone, an amide and, where appropriate, water or a mixture thereof. Examples of alcohols are straight-chain or branched $C_1$–$C_4$-alkyl alcohols, ethylene glycol, polyetheylene glycols of the formula $HO$—$(CH_2$—$CH_2$—$O)_n H$ with n=2 to 1,000 or mixtures of these alcohols with one another or with water, in particular ethylene glycol, mixtures of $C_1$–$C_4$-alkyl alcohols with ethylene glycol or with polyethylene glycols or with water, preferably mixtures of methanol and polyethylene glycols, methanol and ethylene glycol or butanol and water.

Examples of sulfoxides are dimethyl sulfoxide and diethyl sulfoxide.

Mention should be made of sulfolane, (thiolane dioxide) as representative from the sulfone series, and of dimethylformamide, diethylformamide, dimethylacetamide, diethylacetamide and N-methylpyrrolidone as representatives of the amides series.

In a number of cases it is also possible to employ mixtures of alcohols, sulfoxides, sulfolane and/or amides, which may also contain water where appropriate.

Suitable catalysts are palladium or a palladium or nickel compound. It is possible to employ Pd metal, Pd(O) complex compounds, Pd(II) complex compounds, Ni(O) complex compounds and Ni(II) complex compounds, in particular complex compounds which contain phosphines, preferably trisubstituted phosphines such as tri-n-butylphosphine, tri-tert-butylphosphine, triphenylphosphine ($PPh_3$).

Examples of Pd(O) complex compounds are $Pd(PPh_3)_4$, $Pd(dba)_2$.

Examples of Pd(II) complex compounds are $PdCl_2$ $(PPH_3)_2$, $PdBr_2(PPh_3)_2$, $PdCl_2(R''CN)_2 PdBr_2(R''CN)$ with R''=phenyl, methyl, $PdCl_2(dppf)$, $PdBr_2(dppf)$ with dppf=1, 1'-bis(diphenylphosphino)ferrocene, $PdCl_2(COD)$, $PDBr_2$ (COD) with COD=cycloocta-1,5-diene.

Examples of Ni(O) complex compounds are $Ni(PPh_3)_4$ and examples of Ni(II) complex compounds are $NiCl_2$ $(PPh_3)_2$, $NiBr_2(PPh_3)_2$, $NiCl_2 dppf$ and $NiBr_2 dppf$.

It is also possible to employ Pd(II) compounds or Ni(II) compounds, for example corresponding salts, together with the phosphines. In this case, the corresponding complex compounds are formed in situ.

Palladium compounds are particularly suitable, for example $PdCl_2$, $Pd(acetate)_2$.

In the production of [1,1',4',1"]-terphenyl-4-carboxylic acids (R=H in formula (1)) it is advisable for the reaction product formed in the reaction of the biphenyl compound (4) to be treated with water and an acid, in particular a mineral acid, preferably HCl or $H_2SO_4$, in order to bring about or complete hydrolysis of the salts which are formed. It has proved suitable in a number of cases to carry out the hydrolysis at elevated temperatures, for example at 30 to 100° C., in particular at 60 to 90° C.

The present invention also relates to the compounds 4-n-pentoxyphenylboronic acid

trimeric 4-n-pentoxyphenylboronic anhydride

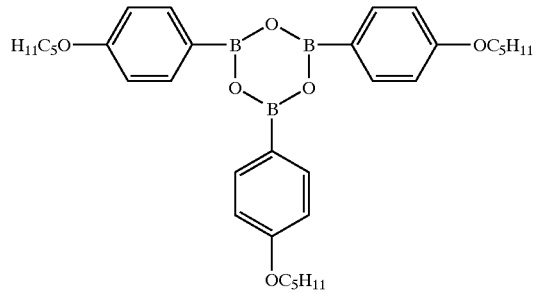

glycol ester of 4-n-pentoxyphenylboronic acid

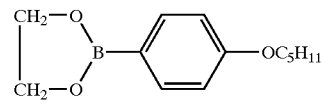

and neopentyl glycolester of 4-n-pentoxyphenylboronic acid

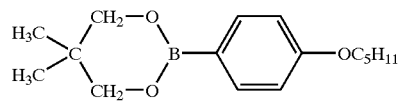

The following examples describe the invention in detail without restricting it.

Experimental part

Preparation of the starting material

EXAMPLES

Example A

Preparation of 4-n-pentoxyphenylmagnesium chloride (starting material).

134 g of a 30% strength solution of 4-pentoxyphenylmagnesium chloride in tetrahydrofuran are introduced together with 60.8 g of magnesium turnings into 178 g of tetrahydrofuran in a standard glass reaction vessel under an inert gas atmosphere and heated to boiling. One tenth of a solution of 497 g of 4-chlorophenyl pentyl ether in 450 g of tetrahydrofuran is added. After the reaction starts, the remaining chloroaromatic compound is added dropwise over the course of 5 hours. After completion of the addition, heating under reflux is continued for 3 hours. After dilution with 675 g of tetrahydrofuran, excess magnesium is filtered off at room temperature under an inert gas atmosphere.

1930 g of a 30% strength solution of 4-pentoxyphenylmagnesium chloride in tetrahydrofuran are obtained.

Preparation of 4-n-pentoxyphenylboronic acid and 4-n-pentoxyphenylboronic anhydride

Example 1

Preparation of a mixture of 4-n-pentoxyphenylboronic acid and trimeric 4-n-pentoxyphenylboronic anhydride 390 g of tetrahydrofuran are introduced together with 437 g of trimethyl borate into a standard glass reaction vessel under an inert gas atmosphere and cooled to −20° C., and 3,000 g of 29% strength solution of 4-pentoxyphenylmagnesium chloride in tetrahydrofuran is added in such a way that the internal temperature does not exceed −15° C. After the addition is complete, the white suspension is cautiously added to a mixture of 1135 g of water and 1135 g of ice, and the resulting mixture is adjusted to pH 1–2 with 325 g of 60% strength sulfuric acid. After the magnesium salts have dissolved, the phases are separated, the upper product-containing organic phase (3200 g) is added to 3 l of water, and the tetrahydrofuran is substantially removed by distillation. This results in a white solid. The boronic acid is filtered off and dried at 50° C./150 mbar. This affords 540 g of 4-pentoxyphenylboronic acid as mixture with the trimeric anhydride, and the acid can be recrystallized from a hydrocarbon (hexane, cyclohexane) for further purification.

Example 2

Preparation of 4-n-pentoxyphenylboronic acid

The pure boronic acid is obtained from the originally obtained mixture of boronic acid with the trimeric anhydride by dissolving the mixture in excess sodium hydroxide at elevated temperature and, after cooling, precipitating the free boronic acid by adding 50% concentrated hydrochloric acid while cooling in ice.

Filtration and washing with water results in 4-n-pentoyphenylboronic acid which is washed with water and has a melting point of 75–80° C. (pressed dry on a tile) and which forms the trimeric anhydride to a certain extent on drying (e.g. in a drying oven).

4-Pentoxyphenylboronic acid: IR spectrum v: 334 (O—H), 2940, 1607, 1413, 1346, 1287, 1259, 1182, 1172, 1158, 1113, 1098, 1021, 997, 818 cm$^{-1}$.

Example 2a

Preparation of trimeric 4-n-pentoxyphenylboronic anhydride

The pure anhydride is obtained from the originally obtained mixture of boronic acid with the trimeric anhydride by either azeotropic dehydration of the mixture in toluene and, after removal of the toluene, subsequent precipitation of the anhydride with cyclopentane, or drying the mixture in a drying oven in vacuo to constant weight at 50° C. The trimeric 4-n-pentoxyphenylboronic anhydride has a melting point of 102–103° C.

4-Pentoxyphenylboronic anhydride: IR spectrum v: 2932, 1604, 1414, 1381, 1368, 1356, 1346, 1305, 1292, 1270, 1247, 1173, 1021, 833 cm$^{-1}$.

Preparation of 4-n-pentoxyphenylboronic esters

Example 3

Preparation of glycol ester of 4-n-pentoxyphenylboronic acid 250 g of 4-n-pentoxyphenylboronic anhydride are dissolved together with 81 g of ethylene glycol by heating in 1,000 ml of toluene. The water produced in the esterification is removed azeotropically with a water trap. After the reaction is complete, firstly the toluene is distilled off and then the residue is fractionally distilled in vacuo. This affords 274 g of glycol ester of 4-n-pentoxyphenylboronic acid of boiling point 156° C./6 mbar, which solidifies after some hours (melting point 37–39° C.).

Example 4

Preparation of neopentyl glycol ester of 4-n-pentoxyphenylboronic acid 505 g of 4-pentoxyphenylboronic anhydride are dissolved together with 274 g of 2,2-dimethylpropane-1,3-diol by heating in 2.5 l of toluene. The water produced in the esterification is removed azeotropically with a water trap. After the reaction is complete, the toluene is completely removed by distillation in vacuo. 550 ml of cyclohexane are added to the residue, and the mixture is heated to boiling, filtered and cooled to room temperature. The precipitated 2,2-dimethylpropane-1,3-diol ester of 4-n-pentoxyphenylboronic acid is filtered off and dried at room temperature in vacuo. 595 g of 2,2-dimethylpropane-1,3-diol ester of 4-n-pentoxyphenylboronic acid (neopentyl glycol ester of 4-n-pentoxyphenylboronic acid) are obtained with melting point 80–80°.

Preparation of 4"-n-pentoxy-[1,1':4',1"]-terphenyl-4-carboxylic acid from 4-n-pentoxyphenylboronic esters Example 5

Preparation of 4"-n-pentoxy-[1,1':4',1"]-terphenyl-4-carboxylic acid 162 g of 4'-iodobiphenyl-4-carboxylic acid are introduced together with 129 g of glycol ester of 4-n-pentoxyphenylboronic acid and 79.5 g of sodium carbonate into 1.5 l of ethylene glycol and, while stirring vigorously, 350 mg of PdCl$_2$(PPh$_3$)$_2$ are added and the mixture is stirred at 80° C. for 6 hours. The hot reaction mixture is cautiously poured into a mixture of 150 g of 37% strength sulfuric acid and 1,000 g of water, and the mixture is heated at 90–100° C. for 30 minutes. After filtration and washing with water, the crude product is dried at 80° C./100 mbar and then recrystallized from dimethylacetamide. This affords after drying 141 g (78%) of 4"-n-pentoxy-[1,1':4',1"]-terphenyl-4-carboxylic acid with a purity of >99%.

Example 6

Preparation of 4"-n-pentoxy-[1,1':4',1"]-terphenyl-4-carboxylic acid 32.4 g of 4'-iodobiphenyl-4-carboxylic acid are introduced together with 25.8 g of glycol ester of 4-n-pentoxyphenylboronic acid and 15.9 g of sodium carbonate into 300 ml of ethylene glycol and, while stirring vigorously, 70 mg of PdCl$_2$(PPh$_3$)$_2$ are added, and the mixture is stirred at 120° C. for 6 hours. The hot reaction mixture is cautiously poured into a mixture of 30 g of 37% strength sulfuric acid and 200 g of water, and the mixture is heated at 90–100° C. for 30 minutes. After filtration and washing with water, the crude product is dried at 80° C./100 mbar and then recrystallized from dimethylacetamide. This affords after drying 25.2 g (70%) of 4"-n-pentoxy-[1,1':4',1"]-4-carboxylic acid with a purity of >99%.

Example 7

Preparation of 4"-n-pentoxy-[1,1':4',1"]-terphenyl-4-carboxylic acid 32.4 g of 4'-iodobiphenyl-4-carboxylic acid are introduced together with 25.8 g of glycol ester of 4-n-pentoxyphenylboronic acid and 15.9 g of sodium carbonate into 300 ml of ethylene glycol and, while stirring vigorously, 18 mg of PdCl$_2$ and 26.6 mg of PPh$_3$ are added, and the mixture is stirred at 80° C. for 6 hours. The hot reaction mixture is cautiously poured into a mixture of 30 g of 37% strength sulfuric acid and 200 g of water, and the mixture is heated at 90–100° C. for 30 minutes. After filtration and washing with water, the crude product is dried at 80° C./100 mbar and then recrystallized from dimethylacetamide. This affords after drying 24.1 g (67%) of 4"-n-pentoxy-[1,1':4',1"]-terphenyl-4-carboxylic acid with a purity of <99%.

Example 8

Preparation of 4"-n-pentoxy-[1,1':4',1"]-terphenyl-4-carboxylic acid 162 g of 4'-iodobiphenyl-4-carboxylic acid are introduced together with 129 g of glycol ester of 4-n-pentoxyphenylboronic acid and 79.5 g of sodium carbonate into 1.5 l of ethylene glycol and, while stirring vigorously, 17.5 ml of a Pd(dba)$_2$ solution are added and the mixture is stirred at 80° C. for 6 hours. The hot reaction mixture is cautiously poured into a mixture of 150 g of 37% strength sulfuric acid and 1,000 g of water, and the mixture is heated at 90–100° C. for 30 minutes. After filtration and washing with water, the crude product is dried at 80° C./100 mbar and then recrystallized from dimethylacetamide. This affords after drying 132 g (73%) of 4"-n-pentoxyterphenyl-4-carboxylic acid with a purity of >99%.

Preparation of the Pd(dba)$_2$ solution:

Under an inert gas, 1.47 g of sodium tetrachloropalladate are suspended in 175 ml of ethylene glycol and heated to 60° C. and, after addition of 3.65 g of dibenzylidine acetone (dba), stirred at 60° C. for 15 minutes. This is followed by addition of 7.5 g of sodium acetate and stirring at room temperature for a further 60 minutes. The dark-colored solution is employed as such.

Example 9

Preparation of 4"-n-pentoxy-[1,1':4',1"]-terphenyl-4-carboxylic acid 20.1 g of 4'-iodobiphenyl-4-carboxylic acid, 13.1 g of sodium carbonate and 21.4 g of glycol ester of 4-n-pentoxyphenylboronic acid are introduced into 260 g of dimethyl sulfoxide (DMSO) and, after addition of 160 mg of PdCl$_2$(PPh$_3$)$_2$, heated at 100–110° C. for 2 hours. The solid is filtered off at 40° C., washed with dimethyl sulfoxide and suspended in 100 ml of water. It is then heated to 80° C., and 47 g of 37% strength sulfuric acid are added dropwise over the course of 1 hour. The mixture is stirred at 80° C. for a further 30 minutes, cooled at 40° C. and filtered. Drying and crystallization from dimethylacetamide results in 18 g (81%) of 4"-n-pentoxy-[1,1':4',1"]-terphenyl-4-carboxylic acid with a purity of >99%.

Example 10

Preparation of 4"-n-pentoxy-[1,1':4',1"]-terphenyl-carboxylic acid 32.4 g of 4'-iodobiphenyl-4-carboxylic acid are introduced together with 25.8 g of glycol ester of 4-n-pentoxyphenylboronic acid and 15.9 g of sodium carbonate into 300 ml of methanol/ethylene glycol 9:1 and, while stirring vigorously, 70 mg of PdCl$_2$(PPh$_3$)$_2$ are added, and the mixture is stirred under reflux for 6 hours. The hot reaction mixture is cautiously poured into a mixture of 30 g of 37% strength sulfuric acid and 200 g of water, and the mixture is heated at 90–100° C. for 30 minutes. After filtration and washing with water, the crude product is dried at 80° C./100 bar and then recrystallized from dimethylacetamide. This affords after drying 28.9 g (80%) of 4"-n-pentoxy-[1,1':4',1"]-terphenyl-4-carboxylic acid with a purity of >99%.

Example 11

Preparation of 4"-n-pentoxy-[1,1':4',1"]-terphenyl-4-carboxylic acid 162 g of 4'-iodobiphenyl-4-carboxylic acid are introduced together with 155 g of 2,2-dimethylpropane-1,3-diol ester of 4-pentoxyphenylboronic acid and 79.5 g of sodium carbonate into 1.5 l of ethylene glycol and, while stirring vigorously, 350 mg of PdCl$_2$(PPh$_3$)$_2$ are added and the mixture is stirred at 80° C. for 6 hours. The hot reaction mixture is cautiously poured into a mixture of 150 g of 37% strength sulfuric acid and 1,000 g of water, and the mixture is heated at 90–100° C. for 30 minutes. After filtration and washing with water, the crude product is dried at 80° C./100 mbar and then recrystallized from dimethylacetamide. This affords after drying 43.2 g (24%) of 4"-n-pentoxyterphenyl-4-carboxylic acid with a purity of >99%.

Example 12

Preparation of 4"-n-pentoxy-[1,1':4',1"]-terphenyl-4-carboxylic acid from 4-n-pentoxyphenylboronic acid 34.1 g (0.1 mol) of 95% pure 4'-iodobiphenyl-4-carboxylic acid are introduced together with 26 g (0.125 mol) of 4-n-pentoxyphenylboronic acid, 15.9 g (0.15 mol) of sodium carbonate and 70 mg of bis(triphenylphosphine) palladium dichloride (PdCl$_2$(PPh$_3$)$_2$) into 300 ml of DMSO. The suspension is stirred at 80° C. for 6 hours, the solid is filtered off, introduced into water, acidified with 37% strength sulfuric acid, heated at 95° C. for 30 minutes and filtered again. Recrystallization from dimethylformamide (DMF) results in 22.1 g (61%) of 4"-pentoxy-[1,1':1',1"]-terphenyl-4-carboxylic acid.

Preparation of methyl 4"-n-pentoxy-[1,1',4',1"]-terphenyl-4-carboxylate from methyl 4'-iodobiphenyl-4-carboxylate Example 13

Preparation of methyl 4"-n-pentoxy-[1,1':4',1"]-terphenyl-4-carboxylate 33.8 g (0.1 mol) of methyl 4'-iodobiphenyl-4-carboxylate are introduced together with 29.3 g (0.125 mol) of glycol ester of 4-n-pentoxyphenylboronic acid, 70 mg of bis(triphenylphosphine)palladium dichloride and 15.9 g (0.15 mol) of sodium carbonate into 300 ml of DMF and stirred at 80° C. for 12 hours. After filtration and washing with water, the dried residue is recrystallized from DMF. This affords 20.5 g (45%) of methyl 4"-n-pentoxy-[1,1':4',1"]-terphenyl-4-carboxylate of melting point 248° C.

Comparative examples according to WO 94/25050 for preparing 4"-n-pentoxy-[1,1':4',1"]-terphenyl-4-carboxylic acid Comparative Example 1

Preparation of 4'-n-pentoxybiphenyl-4-boronic acid from 4-bromo-4'-n-pentoxybiphenyl 31.9 g (0.1 mol) of 4-bromo-4'-n-pentoxybiphenyl are dissolved in 640 ml of tetrahydrofuran under a nitrogen atmosphere and cooled to –78° C., and 67 ml (0.11 mol) of 15% strength solution of n-butyllithium in hexane are added dropwise over the course of 2 hours. During this, the internal temperature is kept in the range from –78° C. to –65° C. After the addition is complete, the thick milky suspension stirred at –78° C. for a further 15 minutes and then 25.5 ml (0.11 mol) of triisopropyl borate are added dropwise at –78° C. over the course of 15 minutes. After the borate addition is complete, the resulting clear solution is stirred at −78° C. for 15 minutes.

This is followed by a removal of the cooling bath and, after 40 minutes, the solution is adjusted to pH 2 with 100 ml of 2N hydrochloric acid. The phases are separated, the organic phase is washed with water and saturated brine and then the solvents are removed by distillation with addition of 200 ml of water. The precipitated solid is filtered off and dried. 25.8 g (91%) of 4'-n-pentoxybiphenyl-4-boronic acid of melting point 148–150° C. are obtained.

Comparative Example 2

Preparation of 4"-pentoxy-[1,1':4',1"]-terphenyl-4-carboxylic acid from 4'-n-pentoxybiphenyl-4-boronic acid 25 g (0.088 mol) of 4'-n-pentoxybiphenyl-4-boronic acid and 21.8 g (0.088 mol) of 4-iodobenzoic acid are suspended under an inert gas atmosphere in a mixture of 270 ml of ethanol, 750 ml of toluene and 132 ml of a 2M sodium carbonate solution and, after addition of 5.08 g (4.4 mmol) of tetrakis(triphenylphosphine)palladium, heated under reflux for 18 hours. The gray-brown mixture is cooled, acidified and extracted with ethyl acetate. The organic phase is washed with water and saturated brine, dried (sodium sulfate) and filtered through Celite. Removal of the solvent results in 1.2 g of a solid which, however, according to HPLC analysis (comparison with reference substance) contains no 4"-n-pentoxy-[1,1':4',1"]-terphenyl-4-carboxylic acid at all.

Evidently, no 4-n-pentoxy-[1,1':4',1"]-terphenyl-4-carboxylic acid has been formed by the synthetic route indicated in WO 92/25050.

What is claimed is:

1. A method for producing [1,1':4',1"]-terphenyl compounds of the formula

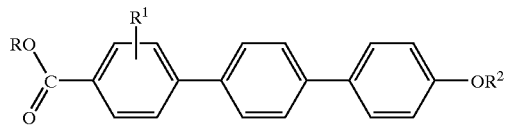

(1)

in which R is hydrogen or a straight-chain or branched $C_1$–$CH_4$-alkyl radical, $R^1$ is hydrogen, a straight-chain or branched $C_1$–$C_4$-alkyl radical or a straight-chain or branched $C_1$–$C_4$-alkoxy radical and $R^2$ is hydrogen, a straight-chain $C_1$–$C_{12}$-alkyl radical, an unsubstituted phenyl radical, a phenyl radical which is substituted by one or two $C_1$–$C_4$-alkyl groups or $C_1$–$C_4$-alkoxy groups, or a radical —$(CH_2)_x$OR$^3$ in which x is an integer from 1 to 4 and $R^3$ is a straight-chain or branched $C_1$–$C_4$-alkyl radical, which comprises reacting a metal aryl and the formula

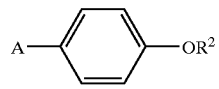

(2)

in which A is a monovalent metal or MeX, where Me is a divalent metal and X is Cl, Br or I, and $R^2$ is A or a trisubstituted silyl radical, or has the meaning indicated in formula (1), excepting hydrogen, with a boric ester at −80 to 40° C. in the presence of an inert solvent, converting the reaction product by hydrolysis into a boronic acid of the formula

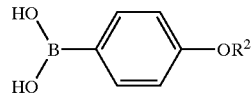

(3)

reacting the boronic acid, a boronic anhydride obtainable from boronic acid by elimination of water, or a mixture of boronic acid and boronic anhydride, with an alcohol, and reacting the boronic ester formed thereby with a biphenyl compound of the formula

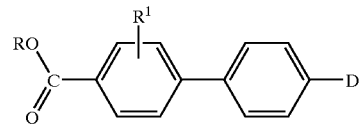

(4)

in which R and $R^1$ have the meaning indicated in formula (1) and D is Cl, Br, I, $O_3S$—$C_nF_{2n+1}$, where n is an integer from 1 to 4, or $N_2^+Y^-$ where $Y^-$ is $ClO_4^-$, $BF_4^-$ or $HSO_4^-$, at 40 to 180° C. in the presence of a catalyst, of an acid-binding agent and of a polar solvent.

2. The method as claimed in claim 1, wherein a metal aryl of the formula (2) in which A is Li, Na, K, MgX or ZnX and X is Cl, Br or I is employed.

3. The method as claimed in claim 1, wherein a metal aryl of the formula (2) in which A, is MgCl, MgBr or MgI is employed.

4. The method as claimed in claim 1, wherein a boric ester $B(OR')_3$ in which R' is identical to or different from one another and is a straight-chain or branched $C_1$–$C_4$-alkyl radical, or a phenyl radical which is unsubstituted or substituted by one or two $C_1$–$C_4$-alkyl groups or $C_1$–$C_4$-alkoxy groups is employed.

5. The method as claimed in claim 1, wherein a dialkyl ether having 1 to 4 carbon atoms in each alkyl radical, a cycloaliphatic ether having 4 to 5 carbon atoms in the ring, a formaldehyde dialkyl acetal, a 1,2-dialkyl glycol ether having 1 to 4 carbon atoms in each alkyl radical, a mixture thereof or a mixture thereof with toluene is employed as inert solvent.

6. The method as claimed claim 1, wherein a $C_1$–$C_8$-alkyl alcohol, a $C_2$–$C_6$-alkane-1,2-diol, a $C_3$–$C_6$-alkane-1,3-diol, a $C_4$–$C_6$-alkane-1,4-diol or 1,2-dihydroxybenzene is employed as alcohol.

7. The method as claimed in claim 1, wherein the boronic acid, the boronic anhydride or the mixture of boronic acid and boronic anhydride is reacted in place of the boronic ester with the biphenyl compound of the formula (4).

8. The method as claimed in claim 1, wherein a biphenyl compound of the formula (4) in which D is Cl, Br, I or $N_2^+Y^-$ is employed.

9. The method as claimed in claim 1, wherein palladium, a palladium compound or a nickel compound is employed as catalyst.

10. The method as claimed in claim 1, where said polar solvent is selected from the group of an alcohol, a sulfoxide, a sulfone, or amide.

11. The method as claimed in claim 1, where said polar solvent is selected from the group of: an alcohol, a sulfoxide, a sulfone, an amide, water or a mixture thereof.

* * * * *